United States Patent
Arita et al.

(10) Patent No.: US 10,577,307 B2
(45) Date of Patent: Mar. 3, 2020

(54) METHODS FOR PRODUCING POLYCYCLIC AROMATIC AMINOPHENOL COMPOUND AND RESIN COMPOSITION, AND POLYCYCLIC AROMATIC AMINOPHENOL COMPOUND, RESIN COMPOSITION, AND CURED PRODUCT

(71) Applicant: DIC Corporation, Tokyo (JP)

(72) Inventors: Kazuo Arita, Sakura (JP); Tomohiro Shimono, Ichihara (JP); Junji Yamaguchi, Tokyo (JP)

(73) Assignee: DIC Corporation, Tokyo (JP)

( * ) Notice: Subject to any disclaimer, the term of this patent is extended or adjusted under 35 U.S.C. 154(b) by 0 days.

(21) Appl. No.: 16/304,429

(22) PCT Filed: Jun. 1, 2017

(86) PCT No.: PCT/JP2017/020417
§ 371 (c)(1),
(2) Date: Nov. 26, 2018

(87) PCT Pub. No.: WO2017/209235
PCT Pub. Date: Dec. 7, 2017

(65) Prior Publication Data
US 2019/0144372 A1 May 16, 2019

(30) Foreign Application Priority Data

Jun. 3, 2016 (JP) ................................. 2016-111864

(51) Int. Cl.
| | |
|---|---|
| *C07C 213/08* | (2006.01) |
| *C07C 215/74* | (2006.01) |
| *C07C 215/86* | (2006.01) |
| *C08G 59/50* | (2006.01) |
| *C07C 215/80* | (2006.01) |
| *C07C 215/76* | (2006.01) |
| *C07C 215/78* | (2006.01) |
| *C08G 59/64* | (2006.01) |
| *C08G 73/06* | (2006.01) |

(52) U.S. Cl.
CPC .......... *C07C 213/08* (2013.01); *C07C 215/74* (2013.01); *C07C 215/76* (2013.01); *C07C 215/78* (2013.01); *C07C 215/80* (2013.01); *C07C 215/86* (2013.01); *C08G 59/50* (2013.01); *C08G 59/64* (2013.01); *C08G 73/0672* (2013.01)

(58) Field of Classification Search
CPC ... C07C 213/08; C07C 215/74; C07C 215/76; C07C 215/78; C07C 215/80; C07C 215/86; C08G 59/50; C08G 59/64; C08G 73/0672
See application file for complete search history.

(56) References Cited

U.S. PATENT DOCUMENTS

| | | | |
|---|---|---|---|
| 4,374,272 A * | 2/1983 | Yuasa | ............... C07C 213/08 558/376 |
| 5,399,715 A | 3/1995 | Naitoh et al. | |
| 6,770,785 B1 | 8/2004 | Desai et al. | |
| 2003/0215734 A1 | 11/2003 | Tsuihiji et al. | |
| 2012/0115764 A1 | 5/2012 | Sabahi et al. | |

FOREIGN PATENT DOCUMENTS

| | | | |
|---|---|---|---|
| CN | 102206495 | * | 10/2011 |
| JP | 2003-327646 A | | 11/2003 |
| JP | 2010-507012 A | | 3/2010 |
| JP | 2010-265185 A | | 11/2010 |
| WO | 93/12933 A1 | | 7/1993 |

OTHER PUBLICATIONS

Pathare et al., "Sulfated tungstate catalyzed selective N-monoalkylation of primary amines with alcohol," Applied Catalysis A: General 452 (2013) 29-33 (Year: 2013).*
Chao et al., "Structure-Guided Design of N-Phenyl Tertiary Amines as Transrepression-Selective Liver X Receptor Modulators with Anti-Inflammatory Activity," J. Med. Chem. 2008, 51, 18, 5758-5765. (Year: 2008).*
English translation of CN102206495, Oct. 5, 2011, pp. 1-28. (Year: 2011).*
International Search Report dated Sep. 5, 2017 issued for PCT/JP2017/020417.

* cited by examiner

*Primary Examiner* — Amy C Bonaparte
(74) *Attorney, Agent, or Firm* — Locke Lord LLP; James E. Armstrong, IV; Nicholas J. DiCeglie, Jr.

(57) ABSTRACT

A task is to provide a method for producing a polycyclic aromatic aminophenol compound through a reduced number of steps at a low cost with high safety. The method for producing a polycyclic aromatic aminophenol compound includes the step of reacting a compound represented by the general formula (1) below and an aromatic amino compound with each other:

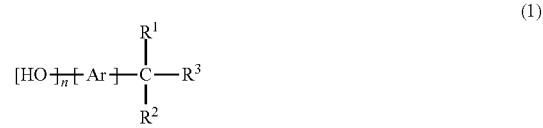

(1)

Wherein n represents an integer of 1 to 8, Ar represents a benzene ring optionally having a substituent, or a naphthalene ring optionally having a substituent, each of $R^1$ and $R^2$ independently represents a hydrogen atom, a hydrocarbon group having 1 to 6 carbon atoms and optionally having a substituent, or an aromatic group optionally having a substituent, and $R^3$ represents a hydroxyl group, a methoxy group, or a halogen atom.

7 Claims, No Drawings

METHODS FOR PRODUCING POLYCYCLIC AROMATIC AMINOPHENOL COMPOUND AND RESIN COMPOSITION, AND POLYCYCLIC AROMATIC AMINOPHENOL COMPOUND, RESIN COMPOSITION, AND CURED PRODUCT

TECHNICAL FIELD

The present invention relates to a method for producing a polycyclic aromatic aminophenol compound and a method for producing a resin composition, and the polycyclic aromatic aminophenol compound and resin composition, and a cured product.

BACKGROUND ART

In recent years, in the electronic device member application, not only metals but also many resin materials are used. The resin materials are lightweight and excellent in moldability, as compared to metals, and therefore the application of the resin materials is expected to be expanded. For meeting demands for such an expanded application, particularly, in the advanced material application, resin materials and compositions are required to be further improved in representative resin performances, such as heat resistance, dielectric properties, and moisture resistance reliability, and to have all these performances and further exhibit high flame retardancy.

For example, as resin materials for electronic device members, thermosetting resins, such as epoxy resins, benzoxazine resins, and BT (bismaleimide-triazine) resins, are used. Particularly, the epoxy resins have high adhesive force and chemical resistance and exhibit low shrinkage upon being cured and high strength, and therefore a great amount of the epoxy resins are used. In an attempt to further improve the heat resistance of the epoxy resin, for example, as described in PTL 1, an epoxy resin having a specific aromatic ring structure has been developed.

An epoxy resin composition can be improved in heat resistance not only by improving the structure of the epoxy resin but also by using a curing agent having a characteristic structure. For example, when using an aromatic aminophenol compound as a curing agent, the epoxy resin composition is improved in heat resistance due to a rigid structure derived from the aromatic structure of the curing agent. Especially when such a curing agent is reacted with an aromatic epoxy resin, the epoxy resin composition can be further improved in heat resistance.

As a conventional method for producing an aromatic aminophenol compound, there can be mentioned the following two methods roughly classified:

1) method in which phenol is subjected to nitration, followed by reduction; and 2) method in which an amino group-containing aromatic compound is reacted with a hydroxyl group-containing or methoxy group-containing aldehyde, followed by reduction.

The aromatic aminophenol compound having a benzene ring which is a monocycle is relatively simple in the structure, and therefore an industrializabe technique for producing the compound has been established, although a nitration step is essential. However, for further improving the heat resistance, when a polycyclic aromatic aminophenol compound having a plurality of benzene rings is produced, a reaction of nitration or reduction is used, and thus a safety problem about the production is caused, and further the polycyclic structure is difficult to maintain due to the stringent reaction conditions for nitration or reduction, making difficult the production of the compound. Further, there is a problem in that the reaction must be conducted through a plurality of steps, increasing the production cost.

Moreover, the conventional methods have a disadvantage in that the design freedom is such small that only a polycyclic aromatic aminophenol compound having a limited structure can be produced.

CITATION LIST

Patent Literature

PTL 1: JP-A-2010-265185

SUMMARY OF INVENTION

Technical Problem

A task of the present invention is to provide a method for producing a polycyclic aromatic aminophenol compound through a reduced number of steps at a low cost with high safety.

Solution to Problem

The present inventors have conducted extensive and intensive studies. As a result, it has been found that the above-mentioned task can be achieved by reacting a hydroxyl group-containing compound having a predetermined structural formula and an aromatic amino compound with each other, and the present invention has been completed.

Specifically, the present invention is directed to a method for producing a polycyclic aromatic aminophenol compound, which includes the step of reacting a compound represented by the general formula (1) below and an aromatic amino compound with each other:

[Chem. 1]

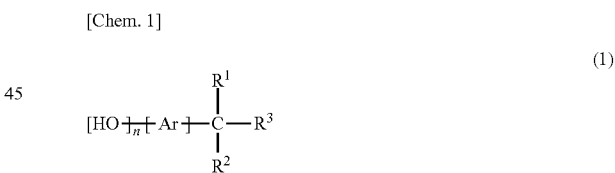

(1)

wherein n represents an integer of 1 to 8, Ar represents a benzene ring optionally having a substituent, or a naphthalene ring optionally having a substituent, each of $R^1$ and $R^2$ independently represents a hydrogen atom, a hydrocarbon group having 1 to 6 carbon atoms and optionally having a substituent, or an aromatic group optionally having a substituent, and $R^3$ represents a hydroxyl group, a methoxy group, or a halogen atom.

Advantageous Effects of Invention

The above-mentioned method for producing a polycyclic aromatic aminophenol compound is advantages in that a polycyclic aromatic aminophenol compound can be produced without using a dangerous step, such as nitration or reduction, through a reduced number of steps, and thus there can be provided a method for producing a polycyclic aromatic aminophenol compound with safety at a low cost.

DESCRIPTION OF EMBODIMENTS

<Method for Producing a Polycyclic Aromatic Aminophenol Compound>

The present invention is directed to a method for producing a polycyclic aromatic aminophenol compound. The method for producing a polycyclic aromatic aminophenol compound of the invention includes the step of reacting a compound represented by the general formula (1) and an aromatic amino compound with each other.

[Compound Represented by the General Formula (1)]

The compound represented by the general formula (1) has the following structure.

[Chem. 2]

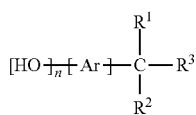

(1)

In the general formula (1), n represents an integer of 1 to 8, and n is preferably 1 to 3.

Ar represents a benzene ring optionally having a substituent, or a naphthalene ring optionally having a substituent. Examples of the substituents for Ar include an alkyl group having 1 to 10 carbon atoms, an alkenyl group having 2 to 10 carbon atoms, an alkynyl group having 2 to 10 carbon atoms, an aryl group having 6 to 10 carbon atoms, an alkoxy group having 1 to 10 carbon atoms, an alkylcarbonyl group having 2 to 10 carbon atoms, an alkyloxycarbonyl group having 2 to 10 carbon atoms, an alkylcarbonyloxy group having 2 to 10 carbon atoms, a halogen atom, a cyano group, a nitro group, an amino group, and a thiol group.

With respect to the alkyl group having 1 to 10 carbon atoms, there is no particular limitation, but examples include a methyl group, an ethyl group, a propyl group, an isopropyl group, a cyclopropyl group, a butyl group, an isobutyl group, a sec-butyl group, a tert-butyl group, a cyclobutyl group, a pentyl group, a 2-methylbutyl group, a 3-methylbutyl group, a hexyl group, a cyclohexyl group, a nonyl group, and a decyl group.

With respect to the alkenyl group having 2 to 10 carbon atoms, there is no particular limitation, but examples include a vinyl group, an allyl group, a propenyl group, an isopropenyl group, a 1-butenyl group, a 2-butenyl group, a 3-butenyl group, a 1-hexenyl group, a 2-hexenyl group, a 3-hexenyl group, a 4-hexenyl group, and a 5-hexenyl group.

With respect to the alkynyl group having 2 to 10 carbon atoms, there is no particular limitation, but examples include an ethynyl group, a propynyl group, a 1-butynyl group, a 2-butynyl group, a 3-butynyl group, a 1-hexynyl group, a 2-hexynyl group, a 3-hexynyl group, a 4-hexynyl group, and a 5-hexynyl group.

With respect to the aryl group having 6 to 10 carbon atoms, there is no particular limitation, but examples include a phenyl group and a naphthyl group.

With respect to the alkoxy group having 1 to 10 carbon atoms, there is no particular limitation, but examples include a methoxy group, an ethoxy group, a propyloxy group, an isopropyloxy group, a butoxy group, a pentyloxy group, a hexyloxy group, and a cyclohexyloxy group.

With respect to the alkylcarbonyl group having 2 to 10 carbon atoms, there is no particular limitation, but examples include a methylcarbonyl group, an ethylcarbonyl group, a propylcarbonyl group, an isopropylcarbonyl group, a butylcarbonyl group, a pentylcarbonyl group, a hexylcarbonyl group, a cyclohexylcarbonyl group, and a nonylcarbonyl group.

With respect to the alkyloxycarbonyl group having 2 to 10 carbon atoms, there is no particular limitation, but examples include a methyloxycarbonyl group, an ethyloxycarbonyl group, a propyloxycarbonyl group, a butyloxycarbonyl group, a hexyloxycarbonyl group, and a cyclohexyloxycarbonyl group.

With respect to the alkylcarbonyloxy group having 2 to 10 carbon atoms, there is no particular limitation, but examples include a methylcarbonyloxy group, an ethylcarbonyloxy group, a propylcarbonyloxy group, a butylcarbonyloxy group, a hexylcarbonyloxy group, and a cyclohexylcarbonyloxy group.

Examples of the halogen atoms include a fluorine atom, a chlorine atom, a bromine atom, and an iodine atom.

The above-mentioned substituents may be contained individually or in combination.

Of these, Ar is preferably a benzene ring optionally having a substituent, more preferably a benzene ring.

Each of $R^1$ and $R^2$ independently represents a hydrogen atom, a hydrocarbon group having 1 to 6 carbon atoms and optionally having a substituent, or an aromatic group optionally having a substituent.

Examples of the hydrocarbon groups having 1 to 6 carbon atoms include an alkyl group having 1 to 6 carbon atoms, an alkenyl group having 2 to 6 carbon atoms, and an alkynyl group having 2 to 6 carbon atoms.

With respect to the alkyl group having 1 to 6 carbon atoms, there is no particular limitation, but examples include a methyl group, an ethyl group, a propyl group, an isopropyl group, a cyclopropyl group, a butyl group, an isobutyl group, a sec-butyl group, a tert-butyl group, a cyclobutyl group, a pentyl group, a 2-methylbutyl group, a 3-methylbutyl group, a hexyl group, and a cyclohexyl group.

With respect to the alkenyl group having 2 to 6 carbon atoms, there is no particular limitation, but examples include a vinyl group, an allyl group, a propenyl group, an isopropenyl group, a 1-butenyl group, a 2-butenyl group, a 3-butenyl group, a 1-hexenyl group, a 2-hexenyl group, a 3-hexenyl group, a 4-hexenyl group, and a 5-hexenyl group.

With respect to the alkynyl group having 2 to 6 carbon atoms, there is no particular limitation, but examples include an ethynyl group, a propynyl group, a 1-butynyl group, a 2-butynyl group, a 3-butynyl group, a 1-hexynyl group, a 2-hexynyl group, a 3-hexynyl group, a 4-hexynyl group, and a 5-hexynyl group.

Examples of the aromatic groups include an aryl group having 6 to 10 carbon atoms and an aralkyl group having 7 to 10 carbon atoms.

Examples of the aryl groups having 6 to 10 carbon atoms include a phenyl group and a naphthyl group.

Examples of the aralkyl groups having 7 to 10 carbon atoms include a benzyl group and a phenethyl group.

The substituents for $R^1$ and $R^2$ are similar to the functional groups shown as examples of the substituents for Ar.

Of these, from the viewpoint of improving the heat resistance, $R^1$ and $R^2$ are preferably a hydrogen atom or a methyl group, more preferably a hydrogen atom.

The above-mentioned $R^3$ represents a hydroxyl group, a methoxy group, or a halogen atom. Of these, $R^3$ is preferably a hydroxyl group from the viewpoint of excellent reactivity.

In an embodiment, preferred is the compound represented by the general formula (1) wherein $R^1$ and $R^2$ are a hydrogen atom and $R^3$ is a hydroxyl group.

As preferred structures of the general formula (1), specifically, there can be mentioned the following structures.

[Chem. 3]

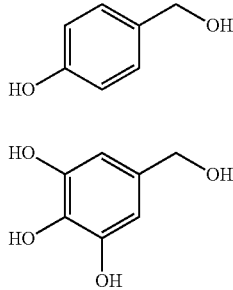

Among the above structures, from the viewpoint of controlling the reactivity, a preferred structure is shown below.

[Chem. 4]

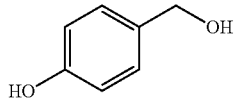

Further, from the view point of the heat resistance, preferred structures are shown below.

[Chem. 5]

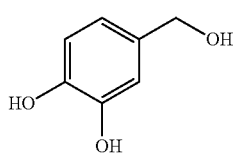 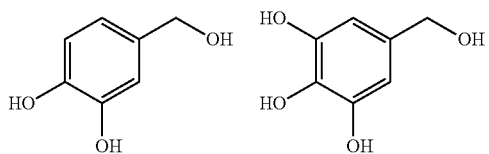

The above-mentioned compounds represented by the general formula (1) may be used individually or in combination.

[Aromatic Amino Compound]

The aromatic amino compound in the invention is a compound having a benzene ring structure and an amino group. In an embodiment, the aromatic amino compound is a compound represented by the general formula (5).

[Chem. 6]

$[H_2N\!-\!Y_1\!\!\xrightarrow{\phantom{x}}_{\!\!m}\!A]$ (5)

In the general formula (5), m represents an integer of 1 to 8, $Y_1$ each independently represents a direct bond or a divalent linking group, and A represents a structure having one or more benzene rings.

With respect to the divalent linking group for $Y_1$ in the formula above, there is no particular limitation, but examples include alkylene having 1 to 6 carbon atoms and alkenylene having 2 to 6 carbon atoms.

Examples of the alkylenes having 1 to 6 carbon atoms include methylene, ethylene, propylene, isobutylene, sec-butylene, tert-butylene, pentylene, iso-pentylene, hexylene, and cyclohexylene.

Examples of the alkenylenes having 2 to 6 carbon atoms include vinylene, 2-butenylene, and 1-butenylene.

The above-mentioned A is a structure having one or more benzene rings. When the A has two or more benzene rings, with respect to the way of bonding the benzene rings, there is no particular limitation, and the benzene rings may be directly bonded to each other, or may be bonded to each other through a linking group, or the benzene rings may be condensed to form a condensed ring, or may together form a spiro ring.

With respect to the linking group for the benzene rings, there is no particular limitation, but examples include divalent linking groups, such as a hydrocarbon group having 1 to 3 carbon atoms, an oxygen atom, a sulfur atom, and a sulfonyl group; and trivalent linking groups, such as a nitrogen atom. Examples of the hydrocarbon groups having 1 to 3 carbon atoms as the linking group include alkylenes, such as methylene, ethylene, ethylidene, propylene, and isopropylidene; and alkenylenes, such as vinylene.

Further, A may have a substituent. Examples of the substituents include a methyl group and a hydroxyl group.

Specific examples of the structures of A include structures represented by the following formulae (6-1) to (6-14).

[Chem. 7]

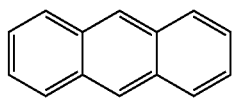 (6-1)

 (6-2)

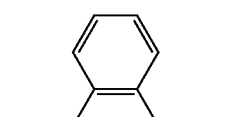 (6-3)

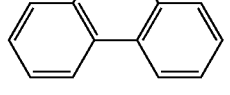 (6-4)

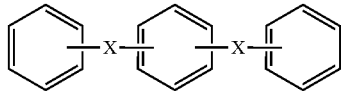 (6-5)

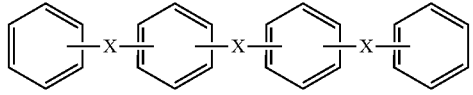 (6-6)

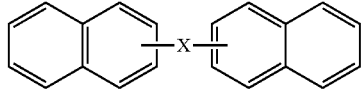 (6-7)

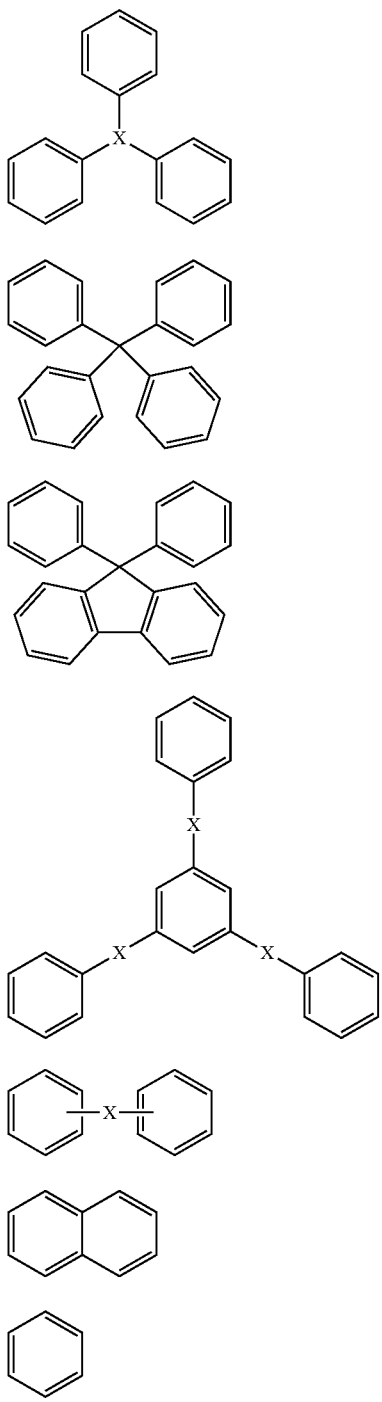

(6-8)
(6-9)
(6-10)
(6-11)
(6-12)
(6-13)
(6-14)

In the formulae (6-1) to (6-14) above, X is a direct bond or a linking group. In the structures represented by the formulae (6-1) to (6-14) above, the benzene ring may have a substituent.

Among the structures represented by the formulae (6-1) to (6-14) above, preferred are the structures of the formulae (6-12) to (6-14) in which the total number of the benzene rings is 1 to 2, further preferred are the structures of the formulae (6-12) and (6-14), and the structure of the formula (6-14) is especially preferred.

As preferred structures of the aromatic amino compound in the invention, there can be mentioned the following structures.

[Chem. 8]

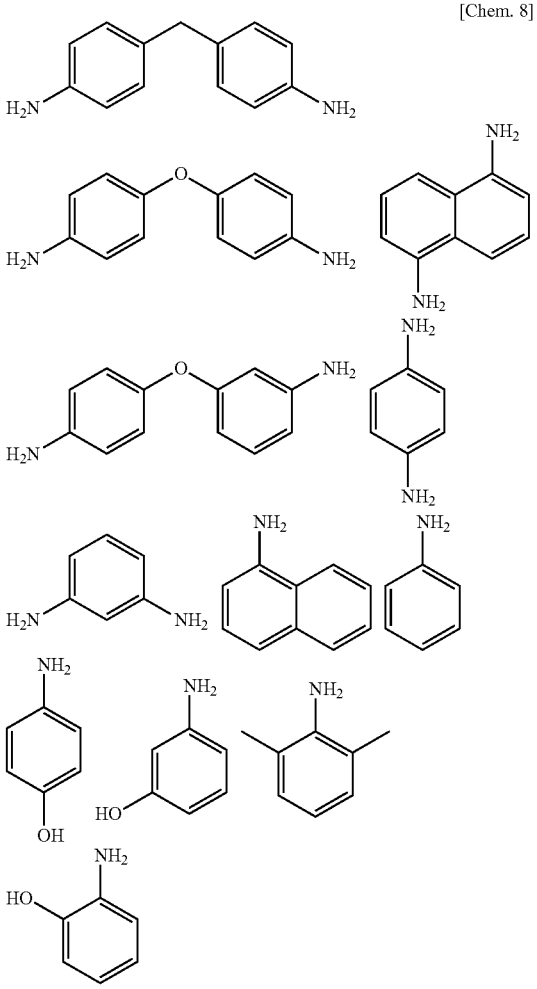

The above-mentioned aromatic amino compounds may be used individually or in combination.

[Reaction]

The polycyclic aromatic aminophenol compound can be obtained by reacting the compound represented by the general formula (1) above and the above-mentioned aromatic amino compound with each other.

A conventional method for producing an aromatic aminophenol compound can be roughly classified into the following two methods:

1) method in which phenol is subjected to nitration, followed by reduction; and 2) method in which an amino group-containing aromatic compound is reacted with a hydroxyl group-containing or methoxy group-containing aldehyde, followed by reduction.

With respect to the method 1) for nitration of phenol, specifically, there can be mentioned a method in which a hydroxyl group-containing aromatic compound is subjected to nitration, followed by reduction.

With respect to the method 2) using an amino group-containing aromatic compound as a starting material, there can be mentioned a method in which an amino group-containing aromatic compound is reacted with a hydroxyl group-containing aromatic aldehyde, followed by reduction, and a method in which an amino group-containing aromatic compound is reacted with a methoxy group-containing aromatic aldehyde, or an amino group- and methoxy group-containing aromatic compound is reacted with an aromatic aldehyde, and then the methoxy group is deblocked to be converted to a hydroxyl group.

In these conventional methods, the reaction for obtaining an aromatic aminophenol compound must be conducted through complicated steps, and therefore likely increases the cost. Further, a dangerous operation, such as nitration or reduction, is needed and hence there are many problems to be solved on the industrialization of the methods. Moreover, the design freedom of the product is small.

In contrast, by using the above-mentioned reaction, a polycyclic aromatic aminophenol compound can be produced through a shortened step, so that the cost can be reduced. Further, the production of the polycyclic aromatic aminophenol compound requires neither nitration nor reduction, and therefore can be easily industrialized. Furthermore, the design freedom of the product is high, making it possible to produce a polycyclic aromatic aminophenol compound having a structure which has not conventionally been known.

The mechanism of this reaction has not yet been elucidated, but $R^3$ (a hydroxyl group, a methoxy group, or a halogen atom) of the compound represented by the general formula (1) and a hydrogen atom bonded to the aromatic ring of the aromatic amino compound are reacted with each other to obtain a polycyclic aromatic aminophenol compound. In this case, the $R^3$ can suffer elimination through the reaction.

More specifically, this reaction can be conducted by heating a mixture obtained by mixing the compound represented by the general formula (1) and the aromatic amino compound with each other.

(Mixture)

The mixture contains the compound represented by the general formula (1) and the aromatic amino compound. If necessary, the mixture may further contain a catalyst, a solvent, or the like.

Compound Represented by the General Formula (1)

With respect to the compound represented by the general formula (1), those which are described above can be used.

The amount of the compound represented by the general formula (1) used may be an arbitrary proportion, based on the mass of the mixture, in terms of solids, but is preferably 5 to 95% by mass, more preferably 20 to 80% by mass. When the amount of the compound represented by the general formula (1) used is 5% by mass or more, the aromatic ring concentration of the product is increased, and this advantageously contributes to an improvement of the heat resistance. On the other hand, when the amount of the compound represented by the general formula (1) used is 95% by mass or less, the fluidity of the product can be advantageously maintained while exhibiting an effect in improving the heat resistance.

Aromatic Amino Compound

With respect to the aromatic amino compound, those which are described above can be used.

Further, in an embodiment, the total of the amount of the compound represented by the general formula (1) used and the amount of the aromatic amino compound used is preferably 80% by mass or more, preferably 90% by mass or more, further preferably 95 to 100% by mass, based on the mass of the mixture, in terms of solids. In other words, in the reaction in this step, the total of the amount of the compound represented by the general formula (1) used and the amount of the aromatic amino compound used is 100% by mass, that is, the reaction can be conducted without using a catalyst. This can remove problems accompanying a catalytic reaction, such as heavy metal pollution, and recovery of the catalyst from the ultimate products.

Catalyst

With respect to the catalyst, there is no particular limitation, but hydrochloric acid, oxalic acid, paratoluenesulfonic acid, or the like can be used.

The amount of the catalyst used is preferably 20% by mass or less, more preferably 10% by mass or less, further preferably 0 to 5% by mass, based on the mass of the mixture, in terms of solids. That is, as mentioned above, the reaction in this step can be conducted without using a catalyst.

(Heating)

With respect to the heating conditions, there is no particular limitation. In an embodiment, there can be mentioned a method in which the mixture is heated so as to be in a molten state, and subjected to reaction while subjecting it to dehydration.

The heating temperature is not particularly limited, but is preferably 80 to 180° C., more preferably 100 to 160° C. When the heating temperature is 80° C. or higher, the reaction time can be advantageously reduced. On the other hand, when the heating temperature is 180° C. or lower, a side reaction, such as a dehydration reaction caused between one compound of the general formula (1) and another one, can be advantageously suppressed.

The heating time is not particularly limited, but is preferably 30 minutes to 15 hours, more preferably 2 to 10 hours. When the heating time is 30 minutes or more, the reaction advantageously achieves a reaction conversion which considerably contributes to an improvement of the product in heat resistance. On the other hand, when the heating time is 15 hours or less, a side reaction, such as a dehydration reaction caused between one compound of the general formula (1) and another one, can be advantageously suppressed.

<Polycyclic Aromatic Aminophenol Compound>

According to an embodiment of the invention, a polycyclic aromatic aminophenol compound is provided. The polycyclic aromatic aminophenol compound obtained by the method of the invention is not formed from only a structure in which the number of phenolic hydroxyl groups and the number of amino groups are the same on the same nucleus, and therefore can exhibit high heat resistance while maintaining the fluidity.

In an embodiment, the polycyclic aromatic aminophenol compound is represented by the following general formula (2).

[Chem. 9]

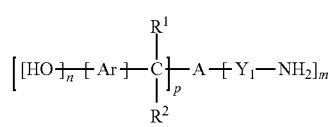

(2)

In the general formula (2), each of n and m independently represents an integer of 1 to 8, p represents an integer of 1 to 7, Ar represents a benzene ring optionally having a substituent, or a naphthalene ring optionally having a substituent, each of $R^1$ and $R^2$ independently represents a hydrogen atom, a hydrocarbon group having 1 to 6 carbon atoms and optionally having a substituent, or an aromatic group optionally having a substituent, $Y_1$ represents a direct bond or a divalent linking group, and A represents a structure having one or more benzene rings.

That is, n, Ar, $R^1$, and $R^2$ are derived from the compound represented by the general formula (1) above, and m, A, and $Y_1$ are derived from the compound represented by the general formula (5) above.

In an embodiment, the polycyclic aromatic aminophenol compound is preferably a compound represented by any one of the following formulae (2-1) to (2-5).

[Chem. 10]

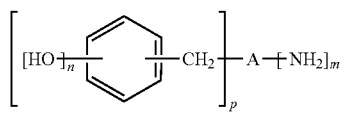
(2-1)

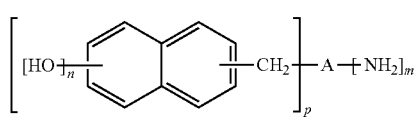
(2-2)

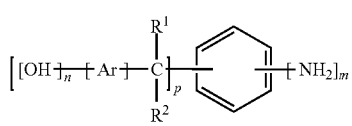
(2-3)

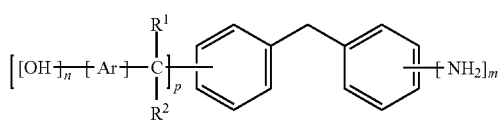
(2-4)

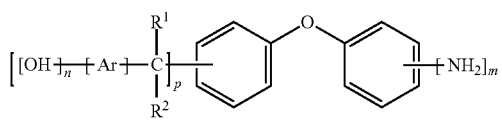
(2-5)

In the formulae (2-1) to (2-5) above, n, m, Ar, $R^1$, $R^2$, and A are as defined above. Of these, from the viewpoint of the balance between the fluidity and the heat resistance, the compounds represented by the formulae (2-3) to (2-5) are preferred.

In an embodiment, the polycyclic aromatic aminophenol compound is more preferably a compound represented by any one of the following formulae (3-1) to (3-7).

[Chem. 11]

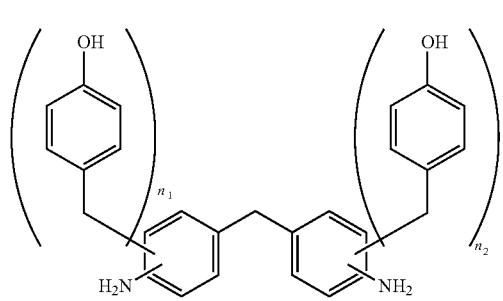
(3-1)

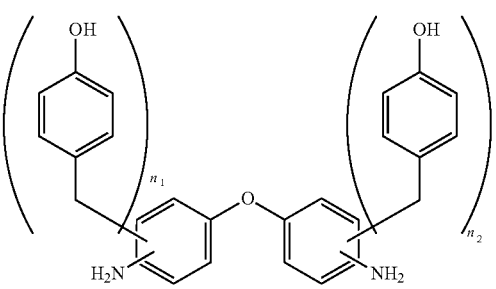
(3-2)

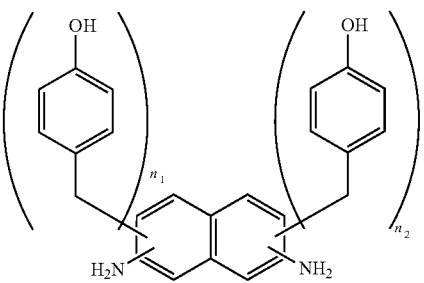
(3-3)

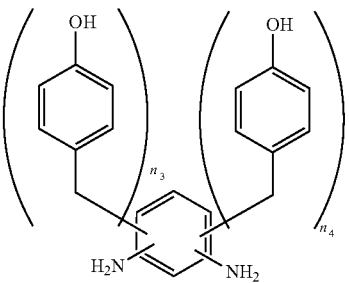
(3-4)

[Chem. 12]

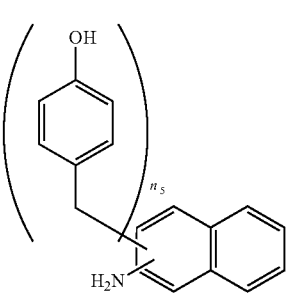
(3-5)

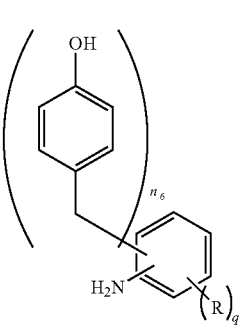
(3-6)

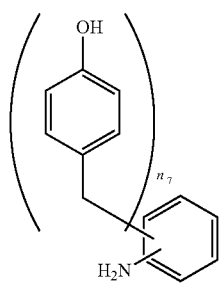

(3-7)

In the formulae (3-1) to (3-7), each of $n_1$ and $n_2$ independently represents an integer of 0 to 4, with the proviso that the relationship: $n_1+n_2 \geq 1$ is satisfied. Each of $n_3$ and $n_4$ independently represents an integer of 0 to 4, with the proviso that the relationship: $4 \leq n_3+n_4 \leq 1$ is satisfied. $n_5$ represents an integer of 1 to 3. R each independently represents a hydroxyl group or a methyl group, and each of $n_6$ and q independently represents an integer of 1 to 4, with the proviso that the relationship: $5 \geq n_6+q \leq 2$ is satisfied. $n_7$ represents an integer of 2 to 5.

Of these, from the viewpoint of the balance between the fluidity and the heat resistance, the compounds represented by the formulae (3-1), (3-2), (3-4), (3-6), and (3-7) are preferred.

Representative examples of structures of the polycyclic aromatic aminophenol compound are shown below.

[Chem. 13]

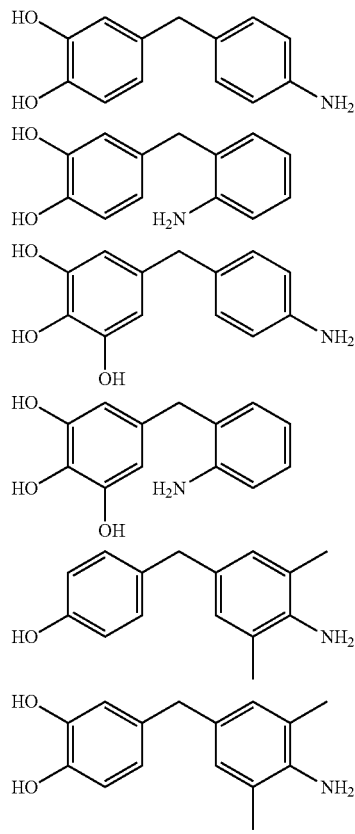

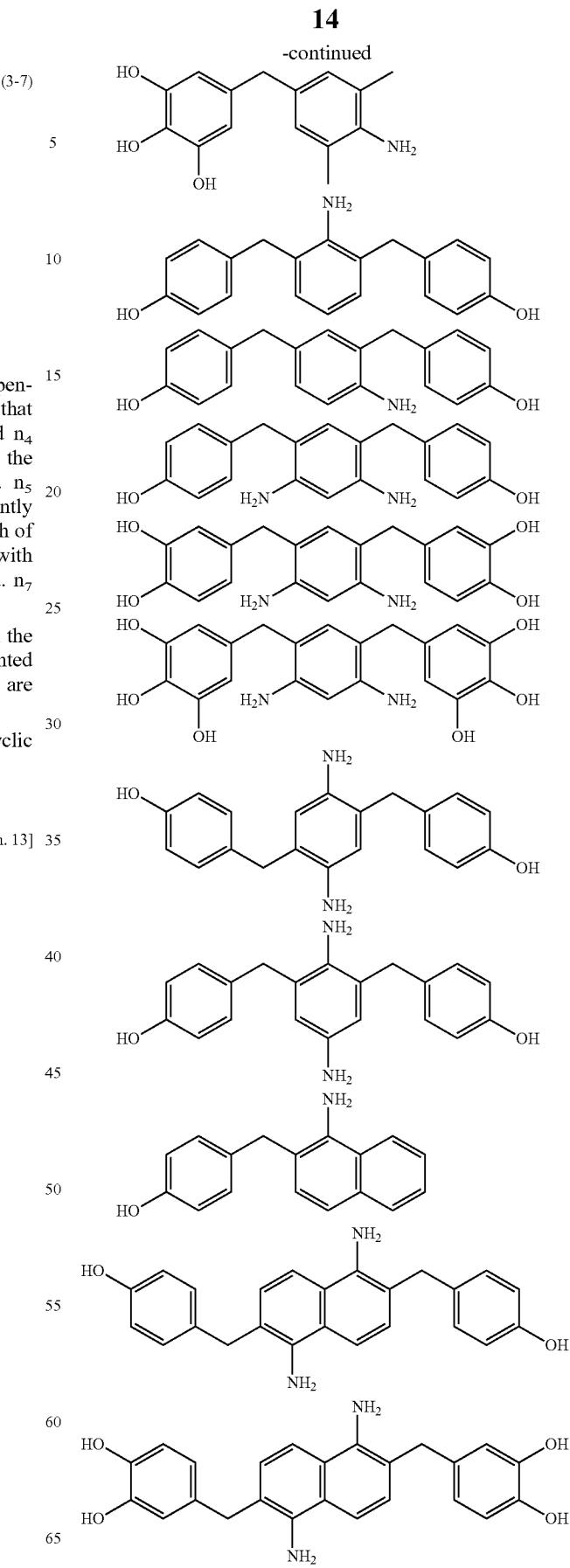

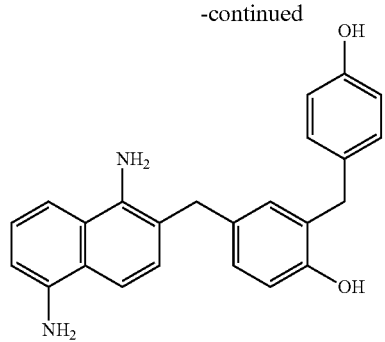
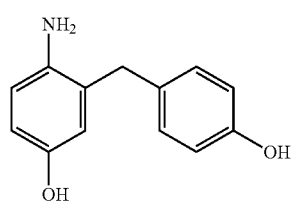
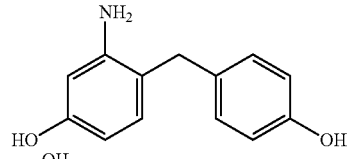
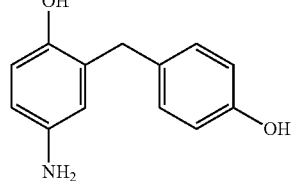
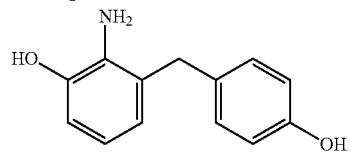
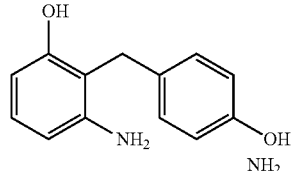
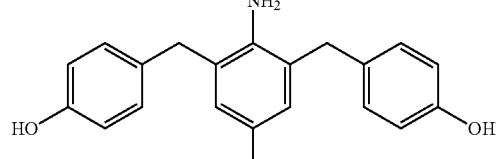
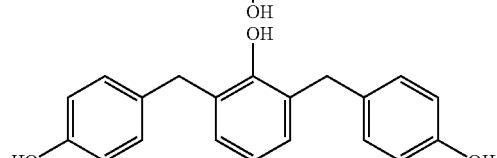
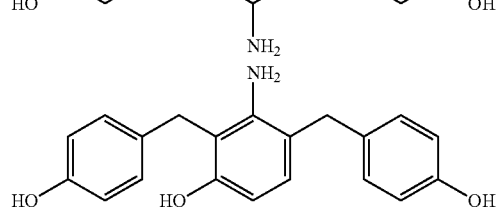
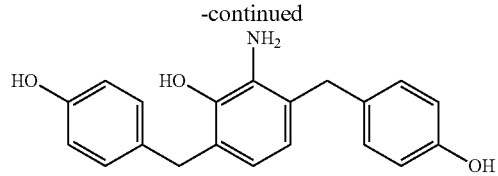
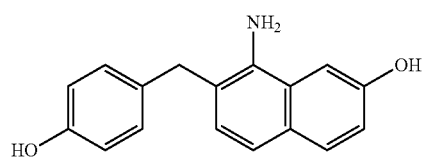
[Chem. 14]
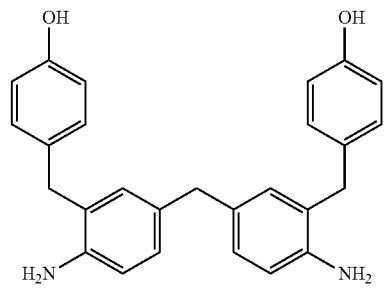
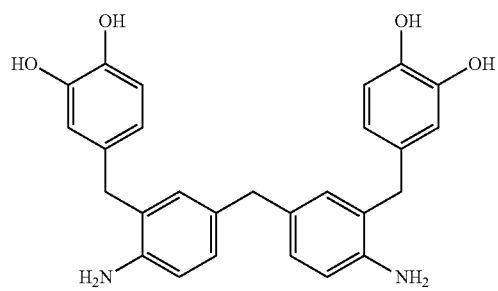
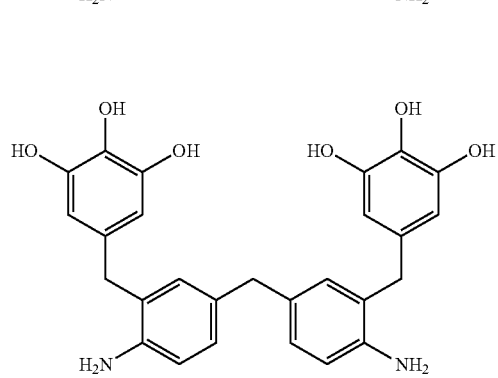
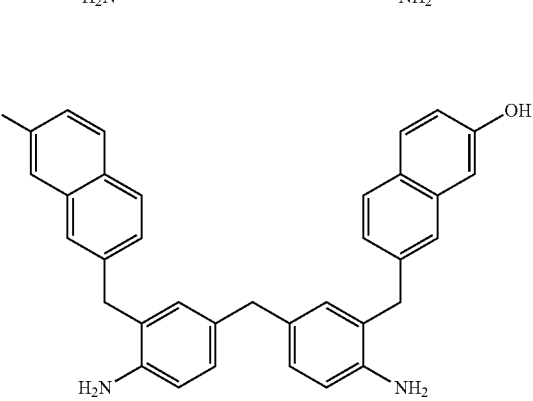

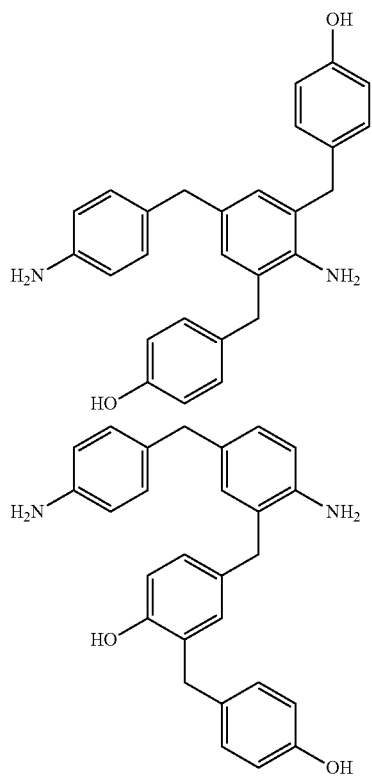
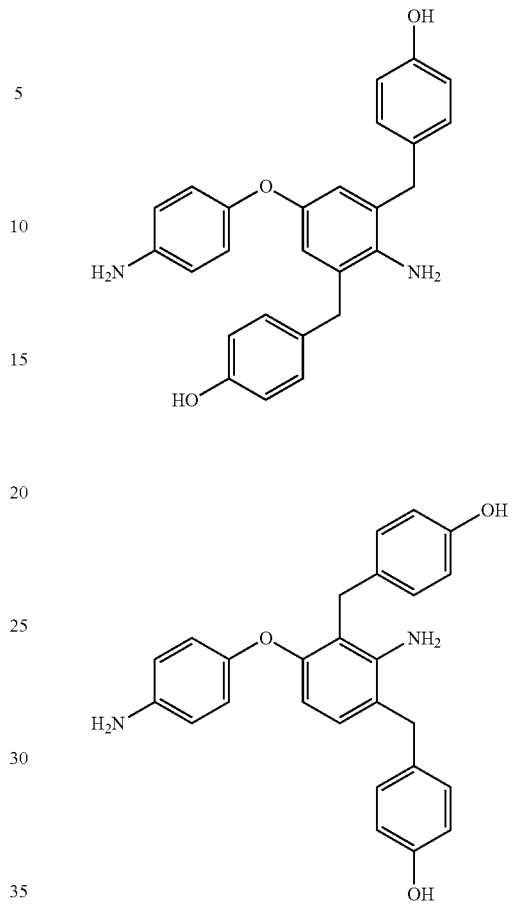
[Chem. 15]
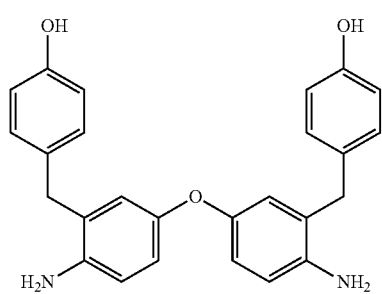
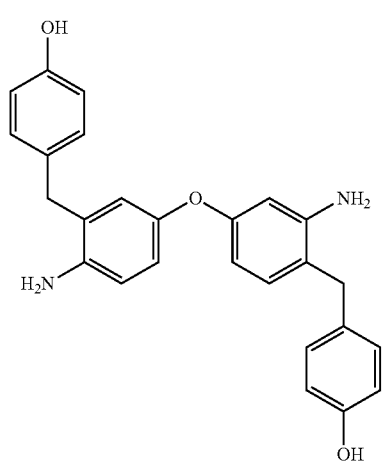

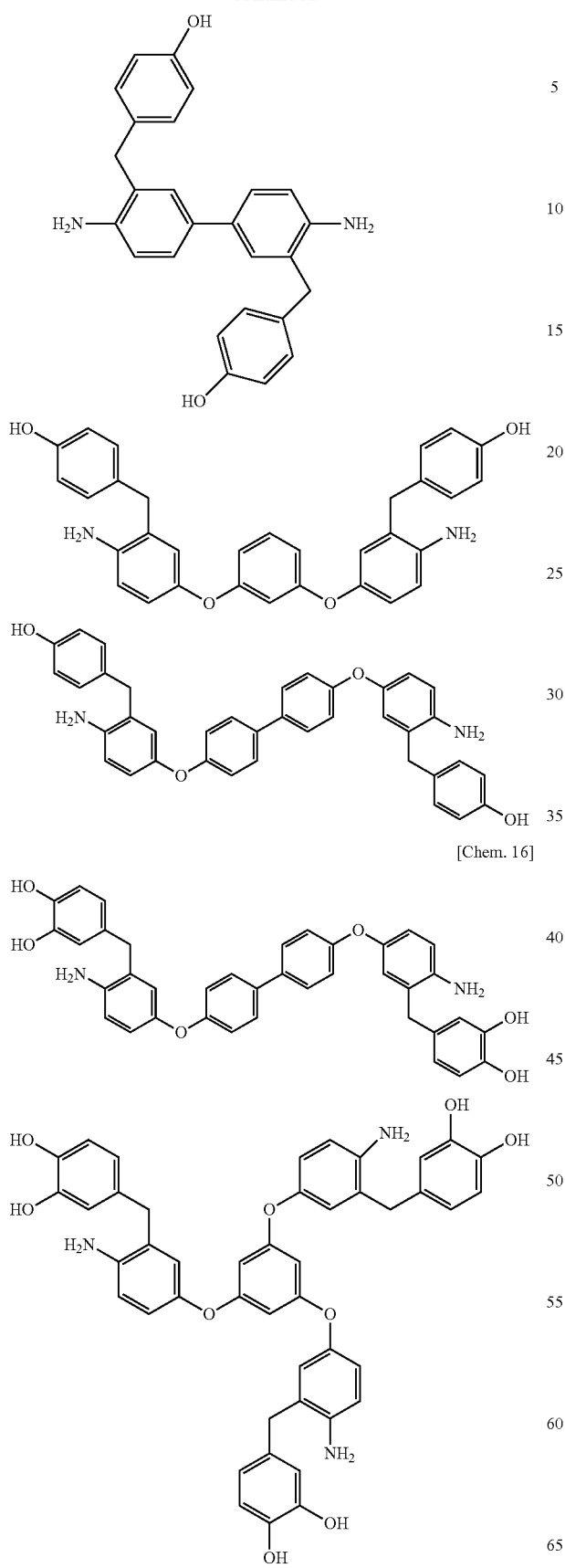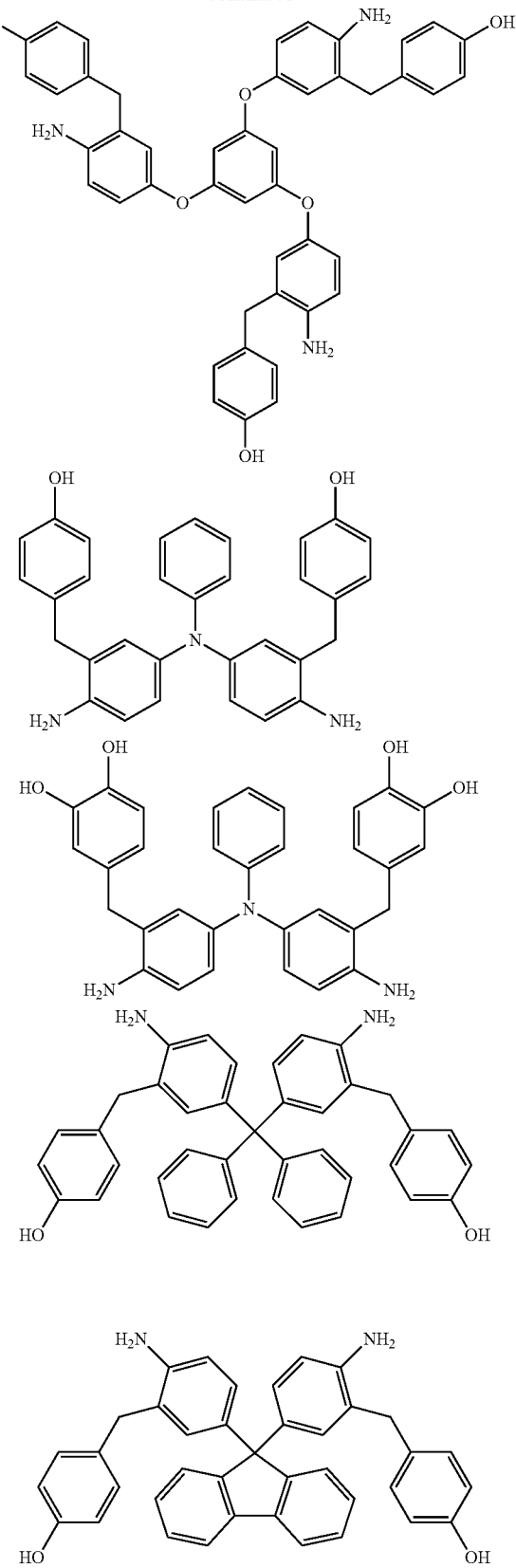
In an embodiment, more preferred structures of the polycyclic aromatic aminophenol compound are shown below.

[Chem. 17]
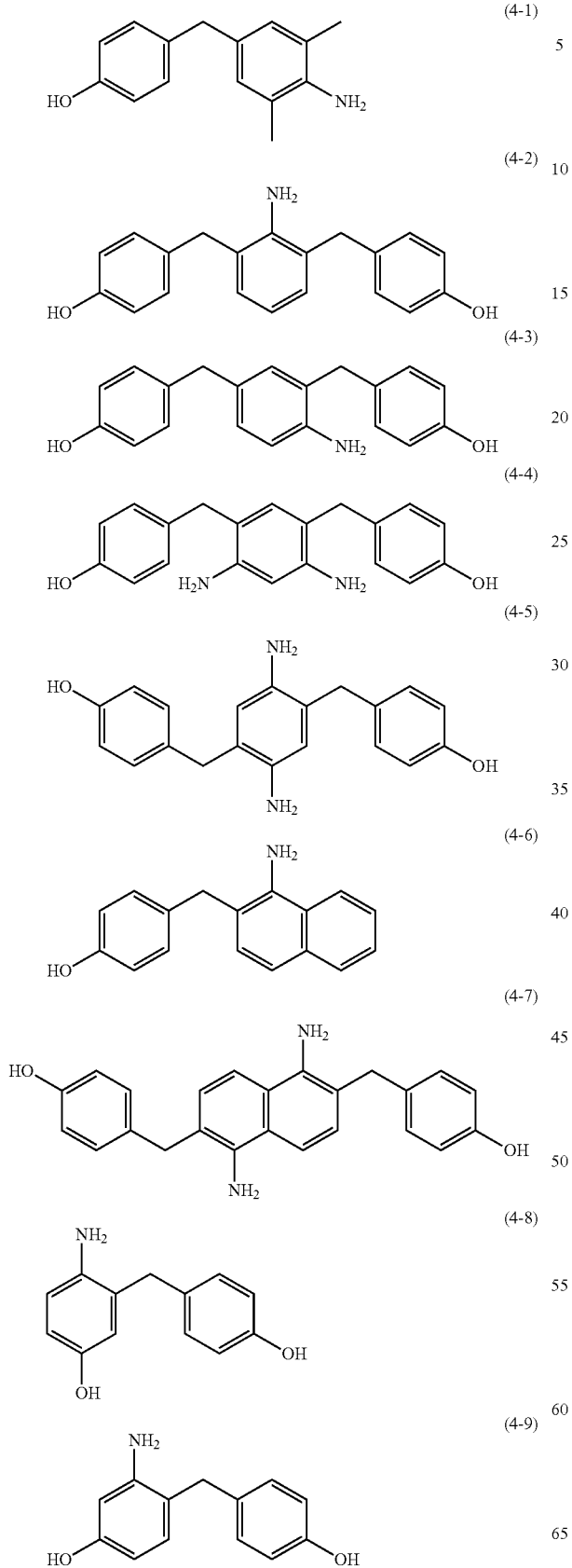
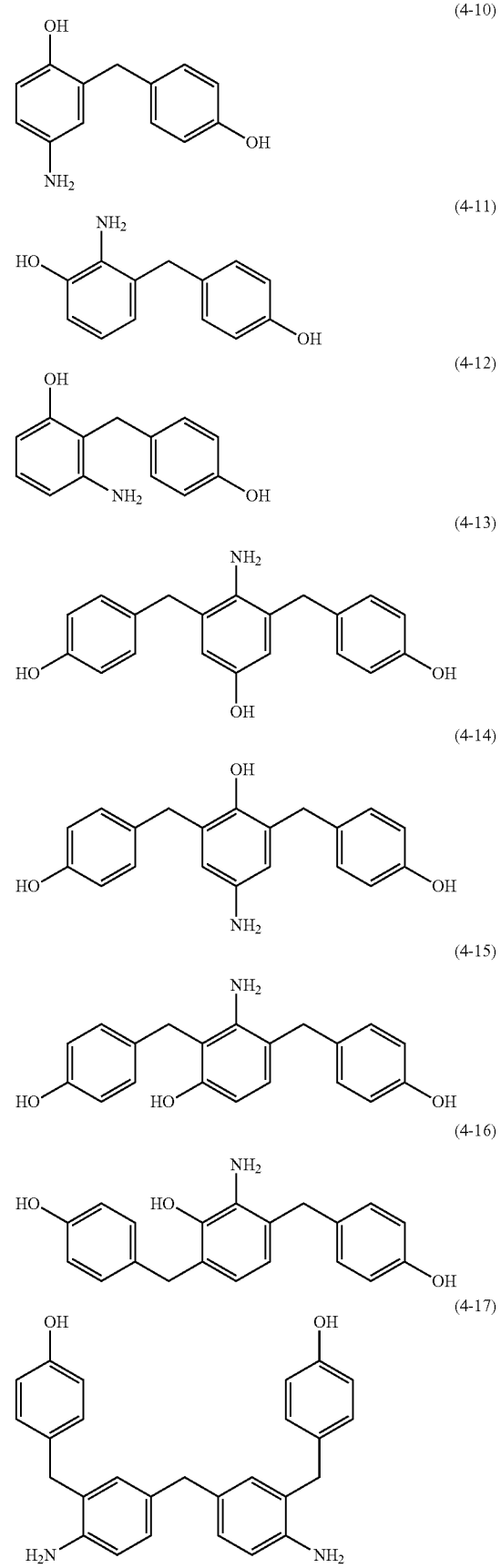

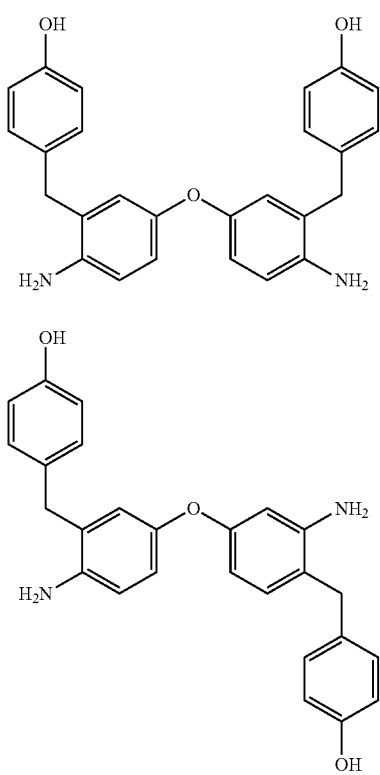
In another embodiment, more preferred structures of the polycyclic aromatic aminophenol compound are shown below.
[Chem. 18]
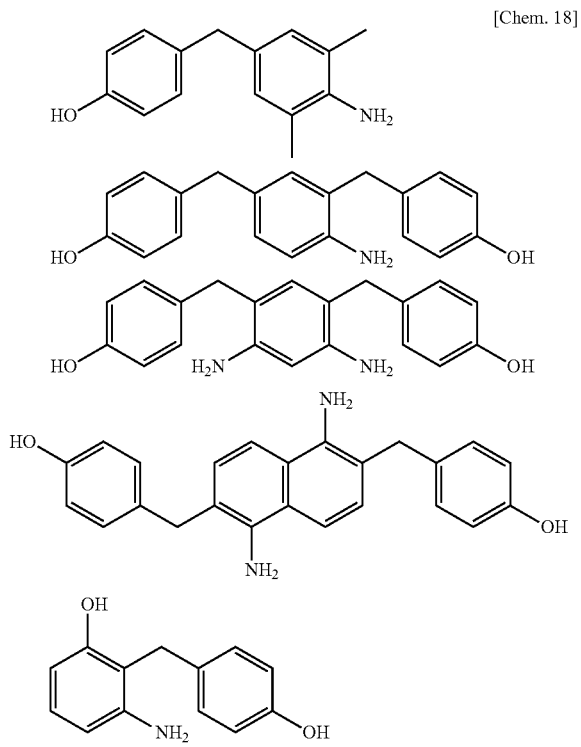
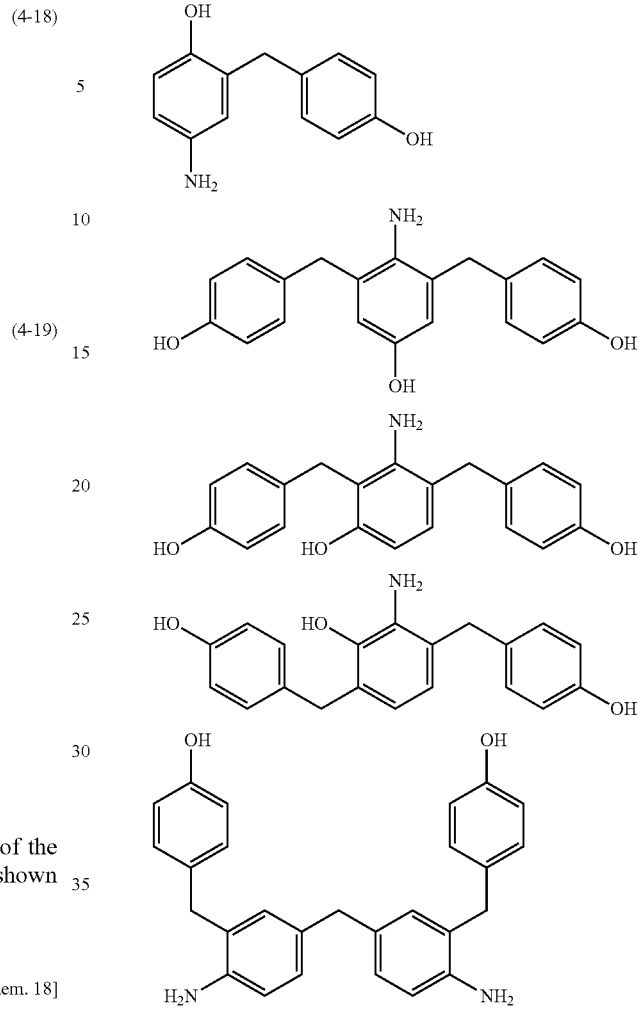
Further preferred structures of the polycyclic aromatic aminophenol compound are shown below.
[Chem. 19]
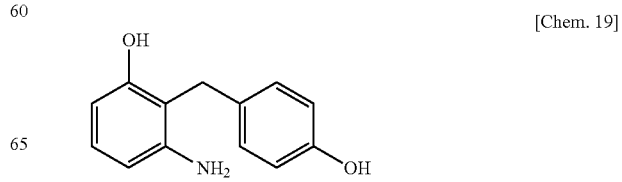

-continued

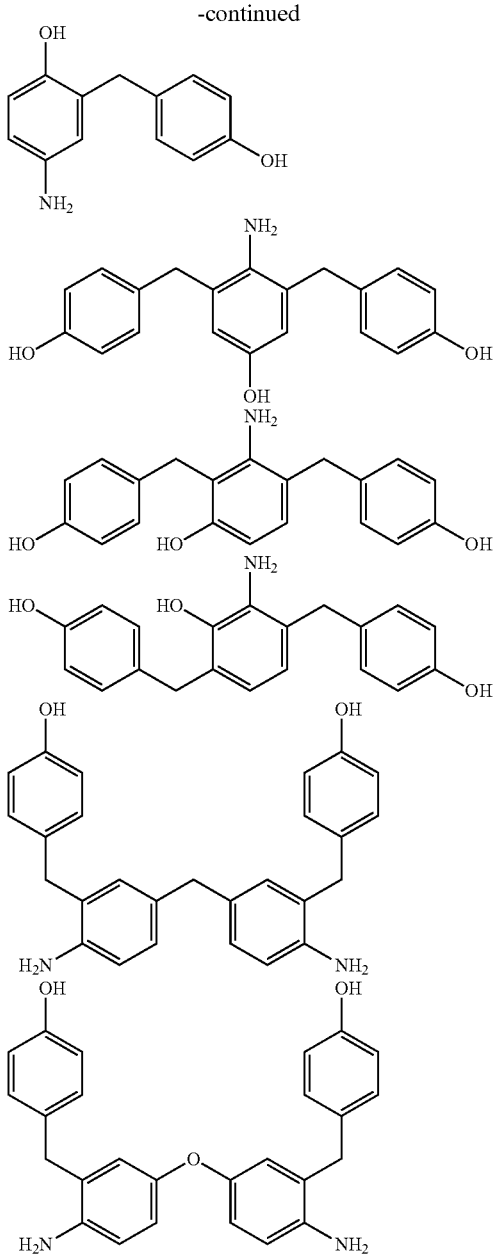

The above-described polycyclic aromatic aminophenol compound is a novel compound which could not be produced by a conventional method. The polycyclic aromatic aminophenol compound has a plurality of aromatic rings, and hence has high heat resistance. Further, the polycyclic aromatic aminophenol compound has an amino group and a hydroxyl group in the molecule thereof, and therefore has high reactivity.

In an embodiment, the polycyclic aromatic aminophenol compound can be applied to the use as a curing agent, a curing catalyst, or a raw material for a thermosetting resin or photo-curable resin.

For example, the polycyclic aromatic aminophenol compound can be used as a resin curing agent for an epoxy resin, a maleimide resin, and the like. The polycyclic aromatic aminophenol compound has high heat resistance, and therefore a cured product obtained by curing the resin can have high heat resistance.

Further, in an embodiment, the polycyclic aromatic aminophenol compound is not formed from only a structure in which the number of phenolic hydroxyl groups and the number of amino groups are the same on the same nucleus, and further the molecule of the compound is collectively poorly symmetrical. Therefore, the polycyclic aromatic aminophenol compound is melted at low temperatures, and can have a low viscosity when being melted, and therefore exhibits excellent handling properties.

In an embodiment, as compared to the polycyclic aromatic aminophenol compound having a structure containing a naphthalene ring, the polycyclic aromatic aminophenol compound having a structure containing a benzene ring is likely to be cured, and the cured product obtained therefrom is likely to have high heat resistance.

<Method for Producing a Resin Composition and Resin Composition>

According to an embodiment of the invention, a method for producing a resin composition is provided.

The method for producing a resin composition has the step of reacting the above-mentioned compound represented by the general formula (1) and aromatic amino compound with each other, and the step of adding a thermosetting resin.

In the method, with respect to the step of adding the resin, there is no particular limitation, and a known method can be appropriately employed.

Further, according to an embodiment of the invention, a resin composition is provided. The resin composition comprises the above-described polycyclic aromatic aminophenol compound and a thermosetting resin. The resin composition may further comprise a curing accelerator, a curing agent other than the polycyclic aromatic aminophenol compound, a thermoplastic resin, a reactive compound, other additives, and the like.

(Thermosetting Resin)

The thermosetting resin indicates a resin having properties such that it can be changed to be substantially insoluble or infusible upon being cured by means of heating, radiation, a catalyst, or the like.

With respect to the thermosetting resin, there is no particular limitation, but examples include an epoxy resin, a maleimide resin, a phenolic resin, an urea resin, a melamine resin, a benzoguanamine resin, an alkyd resin, an unsaturated polyester resin, a vinyl ester resin, a diallyl terephthalate resin, a silicone resin, an urethane resin, a furan resin, a ketone resin, a xylene resin, a thermosetting polyimide resin, a benzoxazine resin, an aniline resin, a cyanate ester, a styrene-maleic anhydride (SMA) resin, and an active ester resin. Of these, the thermosetting resin is preferably an epoxy resin and/or a maleimide resin.

With respect to the epoxy resin, there is no particular limitation as long as the resin has an epoxy group, and examples include a bisphenol A epoxy resin, a bisphenol F epoxy resin, a bisphenol E epoxy resin, a bisphenol S epoxy resin, a bisphenol sulfide epoxy resin, a phenylene ether epoxy resin, a naphthylene ether epoxy resin, a biphenyl epoxy resin, a tetramethylbiphenyl epoxy resin, a polyhydroxynaphthalene epoxy resin, a phenolic novolak epoxy resin, a cresol novolak epoxy resin, a triphenylmethane epoxy resin, a tetraphenylethane epoxy resin, a dicyclopentadiene-phenol addition reaction-type epoxy resin, a phenol aralkyl epoxy resin, a naphthol novolak epoxy resin, a naphthol aralkyl epoxy resin, a naphthol-phenol copolycondensed novolak epoxy resin, a naphthol-cresol copolycondensed novolak epoxy resin, an aromatic hydrocarbon form-aldehyde resin-modified phenolic resin-type epoxy resin, a biphenyl-modified novolak epoxy resin, and an anthracene epoxy resin.

Examples of preferred epoxy resins include epoxy resins having a high aromatic content. The reason for this is that, by virtue of having an aromatic ring, the epoxy resin is improved in heat resistance. As examples of epoxy resins of an especially preferred structure, there can be mentioned a naphthylene ether epoxy resin, a polyhydroxynaphthalene epoxy resin, a biphenyl epoxy resin, and a phenolic aralkyl epoxy resin.

With respect to the maleimide resin, there is no particular limitation as long as the resin has a maleimide group, and examples include m-phenylenebismaleimide, bisphenol A diphenyl ether bismaleimide, 4,4'-diphenyl ether bismaleimide, 4,4'-diphenylmethanebismaleimide, and 3,3'-dimethyl-5,5'-diethyl-4,4'-diphenylmethanebismaleimide. Of these, the maleimide resin is preferably m-phenylenebismaleimide, 4,4'-diphenyl ether bismaleimide, 4,4'-diphenylmethanebismaleimide, or 3,3'-dimethyl-5,5'-diethyl-4,4'-diphenylmethanebismaleimide, more preferably 4,4'-diphenyl ether bismaleimide, 4,4'-diphenylmethanebismaleimide, or 3,3'-dimethyl-5,5'-diethyl-4,4'-diphenylmethanebismaleimide.

The above-mentioned thermosetting resins may be used individually or in combination.

(Curing Accelerator)

In the resin composition of the invention, various types of compounds which accelerate a curing reaction of a thermosetting resin can be used as a curing accelerator. Examples of curing accelerators include a phosphorus compound, a tertiary amine compound, an imidazole compound, an organic acid metal salt, a Lewis acid, and an amine complex salt. Of these, an imidazole compound, a phosphorus compound, or a tertiary amine compound is preferably used, and, especially when used in the semiconductor encapsulation material application, from the viewpoint of achieving excellent curability, heat resistance, electric properties, moisture resistance reliability and the like, triphenylphosphine is preferred as a phosphorus compound, and 1,8-diazabicyclo-[5.4.0]-undecene (DBU) is preferred as a tertiary amine.

(Curing Agent Other than the Polycyclic Aromatic Aminophenol Compound)

Further, in the resin composition of the invention, a curing agent other than the polycyclic aromatic aminophenol compound may be contained. Examples of curing agents other than the polycyclic aromatic aminophenol compound include an amine curing agent, an amide curing agent, an acid anhydride curing agent, a phenolic curing agent, an aminotriazine novolak resin, and an active ester resin.

(Thermoplastic Resin)

Further, in the resin composition of the invention, a thermoplastic resin may be incorporated.

The thermoplastic resin indicates a resin which can be melt-molded by heating. Specific examples of thermoplastic resins include a polyethylene resin, a polypropylene resin, a polystyrene resin, a rubber-modified polystyrene resin, an acrylonitrile-butadiene-styrene (ABS) resin, an acrylonitrile-styrene (AS) resin, a polymethyl methacrylate resin, an acrylic resin, a polyvinyl chloride resin, a polyvinylidene chloride resin, a polyethylene terephthalate resin, an ethylene vinyl alcohol resin, a cellulose acetate resin, an ionomer resin, a polyacrylonitrile resin, a polyamide resin, a polyacetal resin, a polybutylene terephthalate resin, a polylactic acid resin, a polyphenylene ether resin, a modified polyphenylene ether resin, a polycarbonate resin, a polysulfone resin, a polyphenylene sulfide resin, a polyether imide resin, a polyether sulfone resin, a polyarylate resin, a thermoplastic polyimide resin, a polyamide-imide resin, a polyether ether ketone resin, a polyketone resin, a liquid crystalline polyester resin, a fluororesin, a syndiotactic polystyrene resin, and a cyclic polyolefin resin. These thermoplastic resins can be used individually or in combination.

(Reactive Compound)

Further, in the resin composition, a reactive compound may be incorporated. The reactive compound indicates a compound having a reactive group, and may be any of a monomer, an oligomer, and a polymer.

The reactive group may be either a functional group which does not react with the polycyclic aromatic aminophenol compound of the invention or the thermosetting resin in the invention or a functional group capable of reacting with the polycyclic aromatic aminophenol compound or thermosetting resin, but, for further improving the heat resistance, the reactive group is preferably a functional group capable of reacting with the polycyclic aromatic aminophenol compound of the invention or the thermosetting resin in the invention.

Examples of functional groups capable of reacting with the polycyclic aromatic aminophenol compound of the invention or the thermosetting resin in the invention include an epoxy group, a cyanate group, a maleimide group, a phenolic hydroxyl group, an oxazine ring, an amino group, a carboxyl group, an acid anhydride group, an active ester group, a thiol group, and a group having a carbon-carbon double bond or triple bond.

(Other Additives)

In the resin composition, another additive may be added. Examples of other additives include an in organic pigment, an organic pigment, an extender pigment, an organic filler, an inorganic filler, a solvent, clay and a mineral, a wax, a surfactant, a stabilizer, a fluidity modifier, a coupling agent, a dye, a leveling agent, a rheology controlling agent, an ultraviolet light absorber, an antioxidant, a flame retardant, and a plasticizer.

<Cured Product>

According to an embodiment of the invention, a cured product is provided. The cured product is obtained by curing the above-described resin composition.

With respect to the curing method and curing conditions, there is no particular limitation, and those for a known method can be appropriately employed.

The obtained cured product has high heat resistance, and can be advantageously used in the electronic device member application and the like.

EXAMPLES

Hereinbelow, the present invention will be described in more detail with reference to the following Examples and Comparative Examples. In the following Examples and Comparative Examples, "part(s)" and "%" are given by mass unless otherwise specified.

A mass spectrum (FD-MS) was measured under the conditions shown below.

FD-MS apparatus: The measurement was conducted using "JMS-T100GC AccuTOF", manufactured by JEOL LTD.

Measuring range: m/z=50.00 to 2,000.00
Change rate: 25.6 mA/min
Final current value: 40 mA
Cathode voltage: −10 kV

Example 1

A polycyclic aromatic aminophenol compound was synthesized, and an epoxy resin composition and a maleimide resin composition each containing the synthesized compound and a cured product of the epoxy resin composition were produced.
(Synthesis of Polycyclic Aromatic Aminophenol Compound (A-1))

In a 1 L flask equipped with a thermometer, a condenser, a Dean-Stark trap, and a stirrer were charged 198 g (1.00 mol) of 4,4'-diaminodiphenylmethane and 248 g (2.00 mol) of 4-hydroxybenzyl alcohol, and the resultant mixture was heated to 140° C., and stirred while subjecting the mixture in a molten state to dehydration. The mixture was subjected to reaction at the same temperature for 7 hours, and then air-cooled to room temperature to obtain 386 g of a polycyclic aromatic aminophenol compound (A-1) in a solid state (yield: 94.00).

The obtained polycyclic aromatic aminophenol compound (A-1) has the structure shown below.

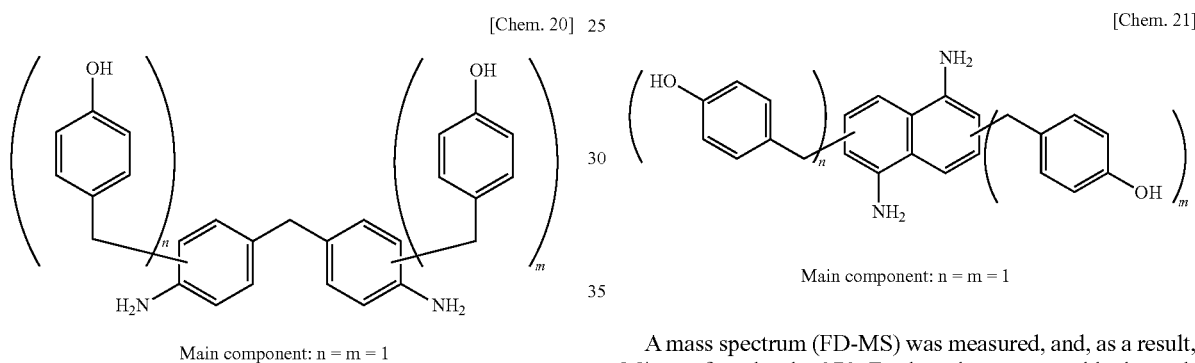

[Chem. 20]

Main component: n = m = 1

A mass spectrum (FD-MS) was measured, and, as a result, $M^+$ was found to be 410. Further, the compound had a melt viscosity of 3.0 dPa·s at 150° C.
(Production of an Epoxy Resin Composition)

25 Parts of the above-obtained polycyclic aromatic aminophenol compound (A-1), 75 parts of N-655-EXP-S which is an epoxy resin (cresol novolak epoxy resin, manufactured by DIC Corporation), and 1 part of triphenylphosphine (TPP, manufactured by Hokko Chemical Industry Co., Ltd.) were mixed with each other to produce an epoxy resin composition.

The epoxy resin composition has a formulation such that the equivalent amount of the epoxy group corresponds to the total of active hydrogens of the amino groups and hydroxyl groups of the polycyclic aromatic aminophenol compound (A-1).
(Production of a Cured Product of the Epoxy Resin Composition)

The above-produced epoxy resin composition was subjected to press molding at 150° C. for 10 minutes, and then heated at 200° C. for 2 hours and then at 250° C. for 2 hours to produce a cured product. The cured product had a plate thickness of 2.4 mm.
(Maleimide Resin Composition)

36 Parts of the above-obtained polycyclic aromatic aminophenol compound (A-1) and 64 parts of BMI-1000 which is a maleimide resin (4,4'-diphenylmethanebismaleimide, manufactured by Daiwa Kasei Industry Co., Ltd.) were mixed with each other to produce a maleimide resin composition.

Example 2

A polycyclic aromatic aminophenol compound was synthesized, and an epoxy resin composition and a maleimide resin composition each containing the synthesized compound and a cured product of the epoxy resin composition were produced.
(Synthesis of Polycyclic Aromatic Aminophenol Compound (A-2))

Substantially the same procedure as in Example 1 was conducted except that, instead of 198 g (1.00 mol) of 4,4'-diaminodiphenylmethane, 158 g (1.00 mol) of 1,5'-diaminonaphthalene was used to obtain 351 g of a polycyclic aromatic aminophenol compound (A-2) in a solid state (yield: 95.0%).

The obtained polycyclic aromatic aminophenol compound (A-2) has the structure shown below.

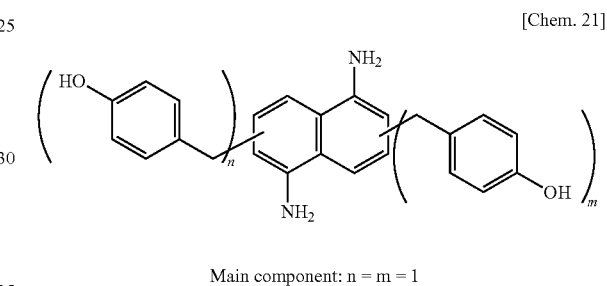

[Chem. 21]

Main component: n = m = 1

A mass spectrum (FD-MS) was measured, and, as a result, $M^+$ was found to be 370. Further, the compound had a melt viscosity of 10.0 dPa·s at 150° C.
(Production of an Epoxy Resin Composition)

23 Parts of the above-obtained polycyclic aromatic aminophenol compound (A-2), 77 parts of N-655-EXP-S, and 1 part of TPP were mixed with each other to produce an epoxy resin composition.

The epoxy resin composition has a formulation such that the equivalent amount of the epoxy group corresponds to the total of active hydrogens of the amino groups and hydroxyl groups of the polycyclic aromatic aminophenol compound (A-2).
(Production of a Cured Product of the Epoxy Resin Composition)

The above-produced epoxy resin composition was cured by the same method as in Example 1 to produce a cured product.
(Maleimide Resin Composition)

34 Parts of the above-obtained polycyclic aromatic aminophenol compound (A-2) and 66 parts of BMI-1000 were mixed with each other to produce a maleimide resin composition.

Example 3

A polycyclic aromatic aminophenol compound was synthesized, and an epoxy resin composition and a maleimide resin composition each containing the synthesized compound and a cured product of the epoxy resin composition were produced.

(Synthesis of Polycyclic Aromatic Aminophenol Compound (A-3))

Substantially the same procedure as in Example 1 was conducted except that, instead of 198 g (1.00 mol) of 4,4'-diaminodiphenylmethane, 109 g of 3-aminophenol (1.00 mol, manufactured by Tokyo Chemical Industry Co., Ltd.) was used, and that the amount of the 4-hydroxybenzyl alcohol used was changed to 124 g (1.00 mol) to obtain 213 g of an aromatic aminophenol compound (A-3) in a solid state (yield: 99%).

The obtained polycyclic aromatic aminophenol compound (A-3) has the structure shown below.

[Chem. 22]

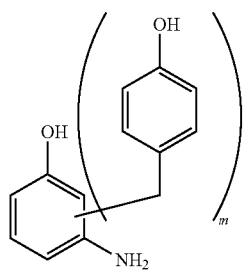

Main component: m = 1

A mass spectrum (FD-MS) was measured, and, as a result, M+ was found to be 215 and 321. Further, the compound had a melt viscosity of 0.8 dPa·s at 150° C.

(Production of an Epoxy Resin Composition)

21 Parts of the above-obtained polycyclic aromatic aminophenol compound (A-3), 79 parts of N-655-EXP-S, and 1 part of TPP were mixed with each other to produce an epoxy resin composition.

The epoxy resin composition has a formulation such that the equivalent amount of the epoxy group corresponds to the total of active hydrogens of the amino group and hydroxyl groups of the polycyclic aromatic aminophenol compound (A-3).

(Production of a Cured Product of the Epoxy Resin Composition)

The above-produced epoxy resin composition was cured by the same method as in Example 1 to produce a cured product.

(Maleimide Resin Composition)

38 Parts of the above-obtained polycyclic aromatic aminophenol compound (A-3) and 62 parts of BMI-1000 were mixed with each other to produce a maleimide resin composition.

Comparative Example 1

4,4'-(1-Methylethylidene)bis[2-aminophenol] was synthesized, and an epoxy resin composition containing the synthesized compound and a cured product of the composition were produced.

Synthesis of 4,4'-(1-methylethylidene)bis[2-aminophenol]

In a 1 L flask equipped with a thermometer, a condenser, and a stirrer, 45 g (0.20 mol) of bisphenol A was dissolved in 225 mL of toluene while stirring, and the inside of the flask was maintained at 0° C. While stirring, 45 mL of concentrated nitric acid (specific gravity: 1.42) was dropwise added to the resultant solution over 2 hours. After completion of the dropwise addition, the resultant mixture was stirred for one hour while cooling it to room temperature. Then, the mixture was further cooled to 0° C. to deposit yellow crystals. The crystals were collected by filtration, and washed with water at 5° C., methanol at 5° C., and diethyl ether at 5° C. in this order to obtain 18.0 g of 4,4'-(1-methylethylidene)bis[2-nitrophenol] in a powder form. On the other hand, the toluene layer separated by filtration was washed until the filtrate became neutral, and then the filtrate was subjected to evaporation under a reduced pressure, and further subjected to vacuum drying at 80° C. for 12 hours to obtain 11.2 g of 4,4'-(1-methylethylidene)bis[2-nitrophenol] in a powder form. The total amount of the both obtained powders was 29.2 g, and the yield was 46%.

In a 1 L flask equipped with a thermometer, a condenser, and a stirrer were charged 29.2 g (0.09 mol) of 4,4'-(1-methylethylidene)bis[2-nitrophenol], 5 g of 10% palladium-supported carbon (Pd/C), and 300 mL of ethanol, and the resultant mixture was stirred at room temperature. The mixture for reaction was heated and subjected to hydrogen reduction reaction in a hydrogen gas atmosphere at 70° C. for 12 hours. The reaction mixture was subjected to filtration, and the resultant filtrate was subjected to evaporation under a reduced pressure, and further subjected to vacuum drying at 80° C. for 12 hours to obtain 19.1 g of 4,4'-(1-methylethylidene)bis[2-nitrophenol] in a powder form (yield: 81%). The total yield calculated from bisphenol A was 37%.

The obtained 4,4'-(1-methylethylidene)bis[2-aminophenol] had a melting point of 278° C., and therefore was not melted at 150° C.

(Production of an Epoxy Resin Composition)

17 Parts of the above-obtained 4,4'-(1-methylethylidene)bis[2-aminophenol], 83 parts of N-655-EXP-S, and 1 part of TPP were mixed with each other to produce an epoxy resin composition.

The epoxy resin composition has a formulation such that the equivalent amount of the epoxy group corresponds to the total of active hydrogens of the amino groups and hydroxyl groups of 4,4'-(1-methylethylidene)bis[2-aminophenol].

(Production of a Cured Product of the Epoxy Resin Composition)

The above-produced epoxy resin composition was cured by the same method as in Example 1 to produce a cured product.

Comparative Example 2

Diaminodiphenylmethane was provided, and an epoxy resin composition and a maleimide resin composition each containing the diaminodiphenylmethane and a cured product of the epoxy resin composition were produced.

(Amino Compound)

Diaminodiphenylmethane was used as an amino compound.

(Production of an Epoxy Resin Composition)

19 Parts of diaminodiphenylmethane, 81 parts of N-655-EXP-S, and 1 part of TPP were mixed with each other to produce an epoxy resin composition.

(Production of a Cured Product of the Epoxy Resin Composition)

The above-produced epoxy resin composition was cured by the same method as in Example 1 to produce a cured product.

(Maleimide Resin Composition)

26 Parts of diaminodiphenylmethane and 74 parts of BMI-1000 were mixed with each other to produce a maleimide resin composition.

[Evaluation of the Epoxy Resin Composition and the Cured Product of the Epoxy Resin Composition]

Using the epoxy resin compositions and the cured products of the epoxy resin compositions produced in Examples 1 to 3 and Comparative Examples 1 and 2, evaluation of the physical properties was conducted.

<Melted at 150° C. or not, and 150° C. Melt Viscosity>

The epoxy resin compositions produced in Examples 1 to 3 and Comparative Examples 1 and 2 were individually heated to 150° C. to examine whether the composition was melted at 150° C. or not.

With respect to the epoxy resin composition which is melted at 150° C., a 150° C. melt viscosity was measured.

The obtained results are shown in Table 1 below.

<Glass Transition Temperature>

Using the cured products produced in Examples 1 to 3 and Comparative Example 2, a glass transition temperature was measured.

(Preparation of a Test Specimen)

A cured product having a thickness of 2.4 mm was cut into a size having a width of 5 mm and a length of 54 mm to prepare a test specimen.

(Measurement of a Glass Transition Temperature)

With respect to the test specimen, using solid viscoelasticity measurement apparatus "DMS 7100" (manufactured by Hitachi High-Tech Science Corporation), a glass transition temperature was measured by DMA (dynamic viscoelasticity measurement). In the measurement, the deformation mode was dual-cantilever bending, and the measurement mode was such that sine wave oscillation was used, the frequency was 1 Hz, and the temperature increase rate was 3° C./minute. A temperature at which the modulus change is the maximum (tan δ change rate is the largest) was evaluated as a glass transition temperature.

The obtained results are shown in Table 1 below.

<Melted at 150° C. or Not>

The maleimide resin composition was heated to 150° C. to examine whether the composition was melted at 150° C. or not. The obtained results are shown in Table 2 below.

TABLE 2

| | Curing agent | | Amount of bismaleimide resin used | Melted or not |
|---|---|---|---|---|
| | Aminophenol compound | Amount | | |
| Example 1 | A-1 | 36 | 64 | Melted |
| Example 2 | A-2 | 34 | 66 | Melted |
| Example 3 | A-3 | 38 | 62 | Melted |
| Comparative Example 2 | 4,4'-(1-Methylethylidene)bis[2-aminophenol] | 26 | 74 | Not melted |

As apparent from the Table 2 above, the maleimide resin compositions produced in Examples 1 to 3 are melted at 150° C. at which it is difficult to melt a bismaleimide resin in an independent form. Thus, these compositions can be processed by molding.

On the other hand, the maleimide resin composition produced in Comparative Example 2 is not melted, and therefore a cured product cannot be obtained from the composition.

INDUSTRIAL APPLICABILITY

The method for producing a polycyclic aromatic aminophenol compound of the present invention is advantageous in that a polycyclic aromatic aminophenol compound can be produced without using a dangerous step, such as nitration or reduction, through a reduced number of steps, and thus there can be provided a method for producing an aromatic aminophenol compound with safety at a low cost. Further, by using the method of the invention, an epoxy resin composition having high heat resistance can be provided.

Furthermore, the method for producing a polycyclic aromatic aminophenol compound of the invention is advanta-

TABLE 1

| | Curing agent | | | Amount of epoxy resin used | Evaluation | | |
|---|---|---|---|---|---|---|---|
| | Aminophenol compound | Amino compound | Amount | | Melted or not | 150° C. Melt viscosity (dPa•s) | Glass transition temperature (° C.) |
| Example 1 | A-1 | — | 25 | 75 | Melted | 1.4 | 268 |
| Example 2 | A-2 | — | 23 | 77 | Melted | 2.1 | 248 |
| Example 3 | A-3 | — | 21 | 79 | Melted | 1.2 | 272 |
| Comparative Example 1 | 4,4'-(1-Methylethylidene)bis[2-aminophenol] | — | 17 | 83 | Not melted | — | No cursed product obtained |
| Comparative Example 2 | — | Diaminodiphenylmethane | 19 | 81 | Melted | 1.8 | 200 |

As apparent from the results shown above, the epoxy resin composition is melted at 150° C., and has a low melt viscosity, and hence is found to have excellent handling properties.

Further, the obtained cured product is found to have high heat resistance.

[Evaluation of the Maleimide Resin Composition]

Using the maleimide resin compositions produced in Examples 1 to 3 and Comparative Example 2, evaluation of the physical properties was conducted.

geous in that the design freedom of the obtained polycyclic aromatic aminophenol compound is high, and therefore a polycyclic aromatic aminophenol compound having a new structure which could not be produced by a conventional method can be produced.

The polycyclic aromatic aminophenol compound obtained by the method of the invention has high heat resistance, and can be especially advantageously used as a curing agent for an epoxy resin and the like.

The invention claimed is:

1. A method for producing a resin composition, the method comprising:

the step of reacting a compound represented by the general formula (1) and an aromatic amino compound with each other to produce a compound represented by the general formula (2); and the step of adding a thermosetting resin to the compound represented by the general formula (2)

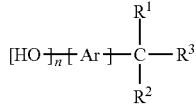
(1)

wherein
n represents an integer of 1 to 8,
Ar represents a benzene ring optionally having a substituent, or a naphthalene ring optionally having a substituent,
each of $R^1$ and $R^2$ independently represents a hydrogen atom, a hydrocarbon group having 1 to 6 carbon atoms and optionally having a substituent, or an aromatic group optionally having a substituent, and
$R^3$ represents a hydroxyl group, a methoxy group, or a halogen atom;

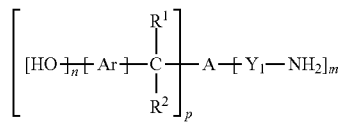
(2)

wherein n, Ar, $R^1$, and $R^2$ are as defined above,
p represents an integer of 1 to 7,
A represents a structure having one or more benzene rings,
$Y_1$ represents a direct bond or a divalent linking group, and
m represents an integer of 1 to 8.

2. A polycyclic aromatic aminophenol compound which is any one of the compounds represented by the following formulae (4-1) to (4-7), (4-10), and (4-12) to (4-19)

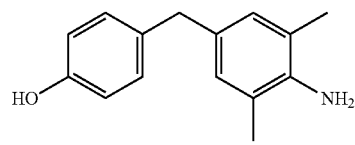
(4-1)

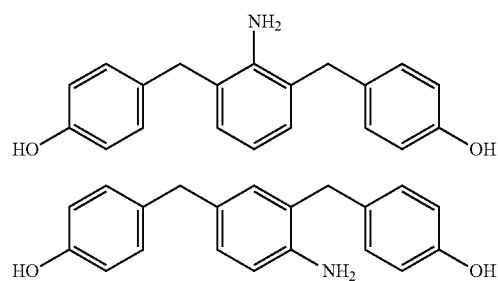
(4-2)

(4-3)

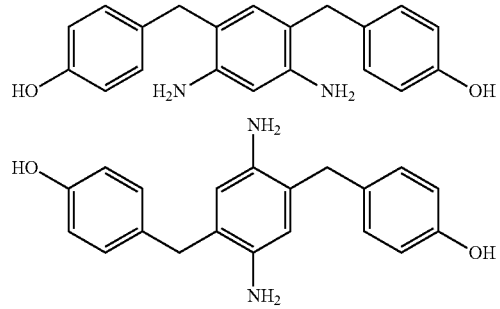
(4-4)

(4-6)

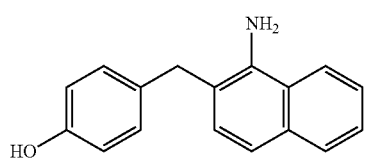
(4-6)

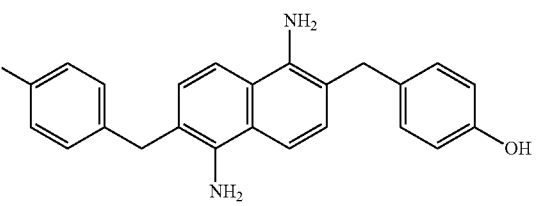
(4-7)

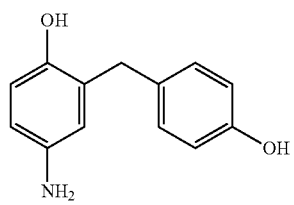
(4-10)

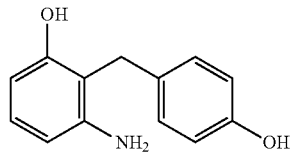
(4-12)

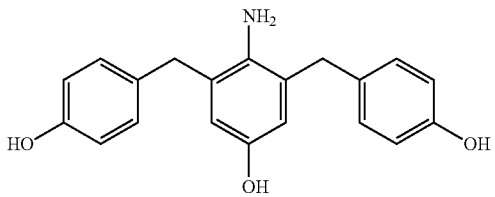
(4-13)

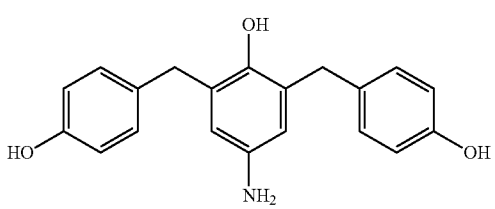
(4-14)

(4-15)
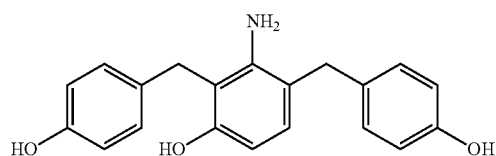

(4-16)
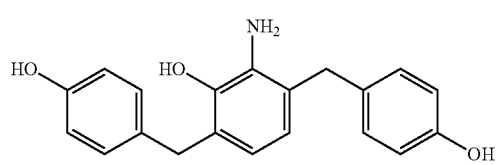

(4-17)
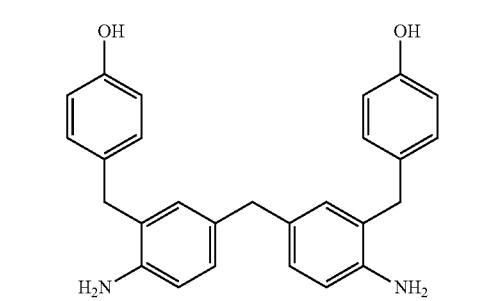

(4-18)
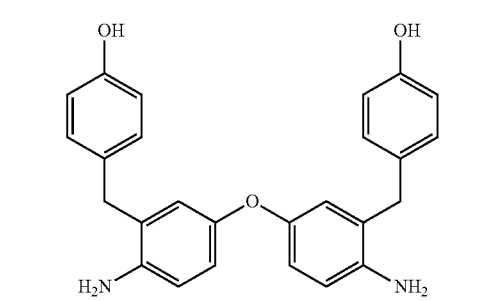

(4-19)
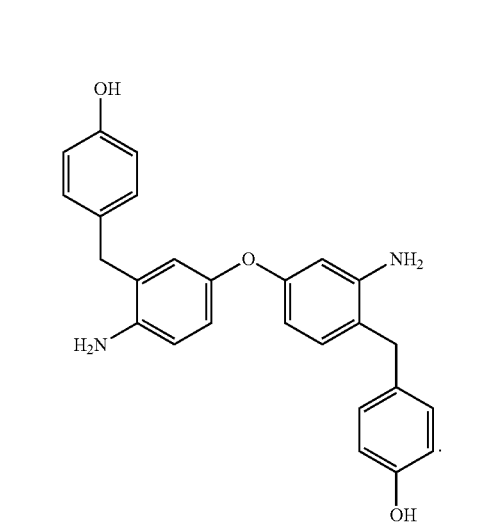

3. A method for producing a polycyclic aromatic aminophenol compound, the method comprising the step of reacting a compound represented by the general formula (1) below and an aromatic amino compound with each other to produce a compound represented by the general formula (2) below:

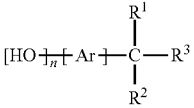 (1)

wherein
n represents an integer of 1 to 8,
Ar represents a benzene ring optionally having a substituent, or a naphthalene ring optionally having a substituent,
$R^1$ and $R^2$ are a hydrogen atom, and
$R^3$ is a hydroxyl group;

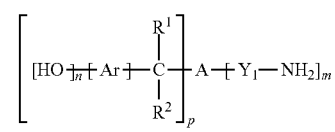 (2)

wherein n, Ar, $R^1$, and $R^2$ are as defined above,
p represents an integer of 1 to 7,
A represents a structure having one or more benzene rings,
$Y_1$ represents a direct bond or a divalent linking group, and
m represents an integer of 1 to 8; and
wherein the reaction in the step uses no catalyst.

4. A resin composition comprising a polycyclic aromatic aminophenol compound which is any one of the compounds represented by the following formulae (4-1) to (4-19):

(4-1)
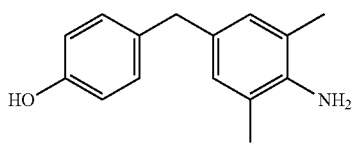

(4-2)
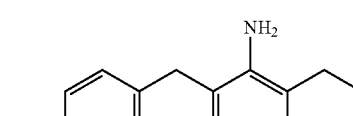

(4-3)
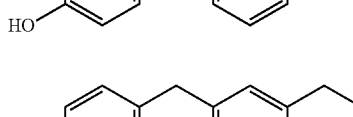

(4-4)
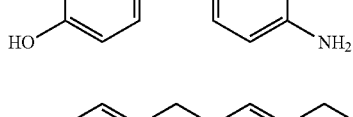

(4-5)
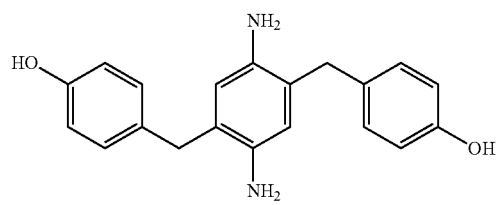
(4-6)
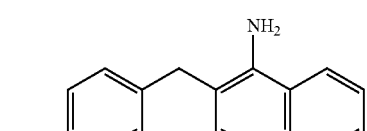
(4-7)
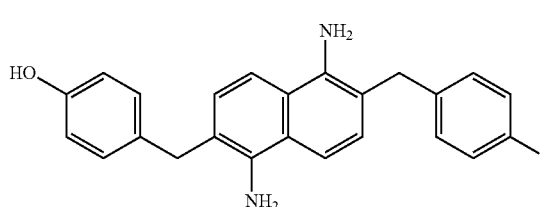
(4-8)
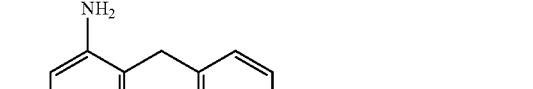
(4-9)
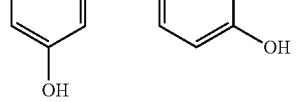
(4-10)
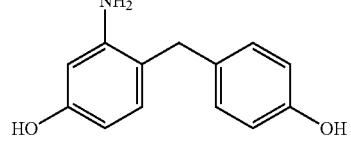
(4-11)
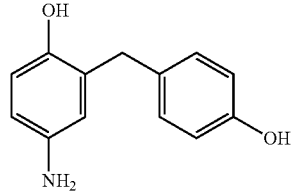
(4-12)
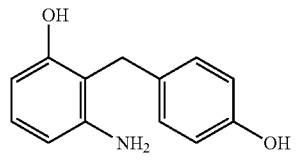
(4-13)
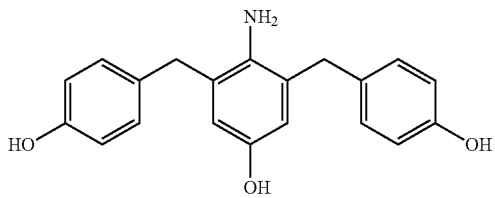
(4-14)
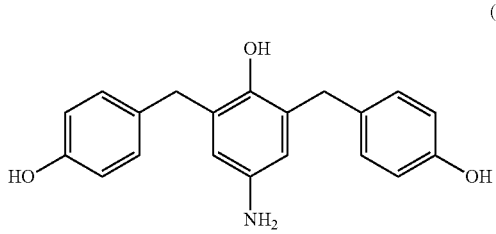
(4-15)
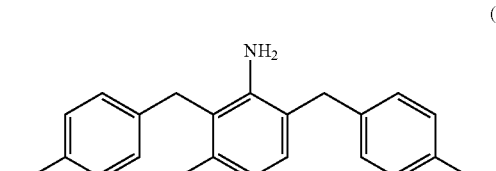
(4-16)
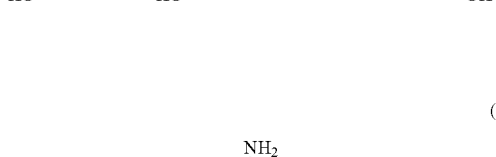
(4-17)
(4-18)
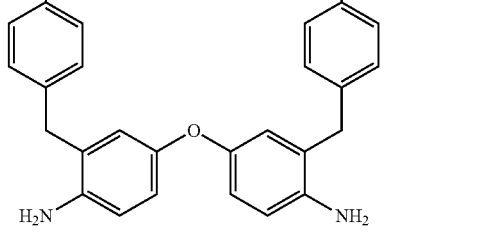

-continued
(4-19)
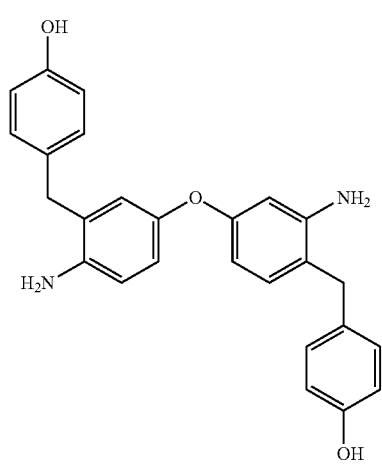
and a thermosetting resin.
5. The resin composition according to claim 4, wherein the thermosetting resin is an epoxy resin and/or a maleimide resin.
6. A cured product comprising a product obtained by curing the resin composition according to claim 4.
7. A cured product comprising a product obtained by curing the resin composition according to claim 5.
* * * * *